United States Patent
Jacobs et al.

[11] Patent Number: 5,924,863
[45] Date of Patent: Jul. 20, 1999

[54] DELIVERY SYSTEM

[76] Inventors: Allison J. Jacobs, 10795 Skinner Rd., NE., Bainbridge Island, Wash. 98110; Stephen Schwendeman, 6346 Hyland Dr., Dublin, Ohio 43107

[21] Appl. No.: 08/872,778

[22] Filed: Jun. 11, 1997

Related U.S. Application Data

[63] Continuation-in-part of application No. 08/811,609, Mar. 5, 1997, Pat. No. 5,769,633, which is a continuation of application No. 08/630,067, Apr. 15, 1996, Pat. No. 5,616,027, which is a continuation of application No. 08/423,895, Apr. 18, 1995, Pat. No. 5,562,449.

[51] Int. Cl.[6] .................................................. A61G 17/02
[52] U.S. Cl. ................................................. 433/80; 433/37
[58] Field of Search ................................... 433/6, 37, 48, 433/80, 216, 215; 128/863

[56] References Cited

U.S. PATENT DOCUMENTS

| | | | |
|---|---|---|---|
| 3,624,909 | 12/1971 | Greenberg | 433/80 |
| 4,428,373 | 1/1984 | Seid et al. | 433/80 X |
| 4,531,914 | 7/1985 | Spinello | 433/80 X |
| 5,011,407 | 4/1991 | Pelerin | 433/48 |
| 5,415,544 | 5/1995 | Oxman et al. | 433/48 |
| 5,503,552 | 4/1996 | Diesso | 433/37 |

*Primary Examiner*—Nicholas D. Lucchesi
*Attorney, Agent, or Firm*—John S. Munday

[57] ABSTRACT

A device useful for delivering a predetermined treatment agent using a non-adhesive carrier for controlled regional release where the relationship between pore size, molecular weight, concentration and the like are predetermined to achieve specific predetermined time and quantity of release. The device includes a mouthguard shaped for extended contact with a substantial portion of the users mouth, such as all of the teeth and gums, for example, so as to provide treatment to a major region of the mouth as opposed to specific topical points of treatment. The mouthguard is held in position by properly fitting it to the patient, such as by softening and molding in situ. The portion of the mouthguard that is in direct contact with the region of treatment is formed from a polymeric material having a network of porous cavities that are sized to incorporate the treatment agent and release that agent over a predetermined period of time. The specific rate of release is controlled by balancing the molecular weight, molecule size, cavity dimensions, and specific properties of the carrying fluid, such as surface tension, solubility and viscosity. Specific preferred treating agents are sodium fluoride for cavity prevention and saliva control agents used during athletic sport participation.

29 Claims, 1 Drawing Sheet

DELIVERY SYSTEM

This is a continuation-in-part of a application filed Mar. 5, 1997, having Ser. No. 08/811,609, now U.S. Pat. No. 5,769,633 which in turn is a continuation of Ser. No. 08/630,067, filed Apr. 15, 1996, now U.S. Pat. No. 5,616,027, which in turn was a continuation of then application having Ser. No. 08/423,895, filed Apr. 18, 1995, now U.S. Pat. No. 5,562,449, issued Oct. 8, 1996.

FIELD OF THE INVENTION

The present invention relates to a system for delivering medicaments and the like to a human. More particularly, this invention relates to a regional application of a controlled release of an agent in the mouth of a patent or user using a non-adhesive carrier. The carrier may be a mouth guard, a liner for a mouth guard or a tray adapted for use in the mouth and the controlled release is intended to take place over a predetermined period of time.

BACKGROUND OF THE INVENTION

The basic concept of applying a treating agent to the mouth of a patient is, of course, not new. Jacobs U.S. Pat. No. 4,044,762 discloses incorporation of fluorides in mouthguards. In this patent an athletic mouthguard is disclosed of a generally U-shaped configuration, into which up to about five percent by weight of a fluoride compound has been added, so that a significant amount of fluoride compound is released to the wearer's teeth during repeated uses. The mouthguard itself is made of a polymer that may be formed by heat into an appropriate shape for direct contact with the teeth and gums. There is no attempt to regulate the rate of release, nor is there any recognition that control of elution is possible. In this patent, in fact, there is no method for controlling the rate of release, nor is there any way to restrict the release to a region of interest.

A number of other patents have been granted on products that are used in a person's mouth to, inter alia, release an agent to the patient. Wallshein U.S. Pat. No. 3,205,576 impregnates the elastic bands used in orthodontic treatment, where the release of the impregnated agent is affected by expansion and contraction of the elastic band. Goodson U.S. Pat. Nos. 4,764377 and 4,982,736 both relate to intra-pocket systems where an elastic band is used to retain the therapeutic agent (such as tetracycline in a polymeric matrix) for localized topical treatment. Damani U.S. Pat. No. 5,114,718 to Proctor & Gamble Company uses strips, chips and cones that are inserted for localized topical treatment as well.

Gunther U.S. Pat. No. 4,243,655 employs chewing gum, mouthwashes, dentifrices and other solutions to provide Biotin-antagonists to the mouth. White U.S. Pat. No. 4,554,154 also has a chewable plastic tape carrying a biologically acceptable adhesive that has been encapsulated. Simone etal U.S. Pat. Nos. 5,296,209 and 5,407,661 to Colgate Palmolive Company both relate to edible pet chew products. Taken together these patents disclose the concept of chewable delivery systems. In addition, Lee U.S. Pat. No. 5,437,872 discloses a tablet or lozenge that is held in the patient's mouth. Snipes U.S. Pat. No. 5,135,752 discloses a buccal dosage form which melts in the oral cavity. Both of these last two patents clearly have a disposable system that does not remain in situ and does not offer prolonged release.

Hollander etal U.S. Pat. No. 3,203,097 discloses a dental cushion formed from flannel cloth, a wax-plasticizer and a germicide. There is no concept of controlled release although data showing prolonged test cultures is disclosed. This patent does not contemplate an additive to the artificial dentures. Shepherd etal U.S. Pat. No. 3,618,213 also discloses denture liners made from cast polymers having additives that are gradually released from the article.

None of the prior art specifically teach the concept of a non-adhesive carrier for controlled regional release where the relationship between pore size, molecular weight, concentration and the like are predetermined to achieve specific predetermined times of release. More specifically, none of the references teach the concept of a mouth guard that releases an agent over the nominal time that the mouthguard might be in use, such as the time in which a game may be played, so that a controlled benefit may be obtained in that period of time. The concept of controlling the time of the agent's release is not taught in the prior art.

Accordingly, it is an object of the present invention to provide a device for introducing agents into the mouth of a person for a specific period of time to accomplish a specific, predetermined purpose.

Another object of this invention is to provide a device which releases a treating agent into the mouth without adhesive attachment to the mouth.

Still another specific object of the present invention is to provide a device for releasing a treatment agent into the mouth under conditions where the quantity and duration of release of the agent are controlled to conform to a predetermined treatment.

A specific object of the present invention is to provide a device capable of releasing a treating agent into the mouth for the specific purpose of controlling the release of saliva by the user.

Other objects will appear hereinafter.

SUMMARY OF THE INVENTION

It has now been discovered that the above and other objects of the present invention may be accomplished in the following manner. Specifically, the present invention provides a device useful for delivering a predetermined treatment agent to a major region of a user's mouth.

The device comprises a mouthguard mounting a non-adhesive carrier for controlled regional release. The carrier is formed from a polymeric material having a network of porous cavities defining a treatment release region. The cavities are sized to incorporate a treatment agent and release this agent over a predetermined period of time. The treating agent in a treating fluid is released from the porous cavities in the treatment release region to provide for release of the agent over a predetermined contact time with a substantial portion of the users mouth.

Release is accomplished because the treating agent has a molecular weight and concentration in the treating fluid such that the specific rate of release of the agent is controlled by the relationship of the molecular weight and molecule size of the agent, the cavity dimensions, and the specific properties of the carrying fluid. Some specific properties of the carrying fluid comprise its surface tension and viscosity, as well as the degree of solubility of the agent.

The mouthguard is held in position by fitting it to the patient.

In one embodiment, the invention comprises a dual tray assembly useful for delivering a predetermined treatment agent to a major region of a user's mouth. The dual tray assembly includes an outer tray and a non-adhesive mouthguard carrier for controlled regional release. This carrier is formed from the material providing the network of porous cavities defining the treatment release region. The carrier in this embodiment will be an inner tray which extends over the teeth and removably nests inside the carrier tray making a dual tray assembly.

The inner tray is made of a thermoplastic compound that is soft and pliable at elevated temperatures but is hard and flexible at body temperatures to conform to the shape of the teeth after the dual tray assembly at elevated temperature is placed in the patient's mouth and is conformed to the shape of the teeth by pressure applied to the inner tray through the dual tray assembly. The preferred inner tray material is a polycaprolactone polymer.

The treating agent may be combined with the inner tray material by soaking to achieve absorption or by admixing during a step in the formation of the thermoplastic compound.

BRIEF DESCRIPTION OF THE DRAWINGS

For a more complete understanding of the invention, reference is hereby made to the drawings, in which.

DETAILED DESCRIPTION OF THE PREFERRED EMBODIMENT

Figure 1:
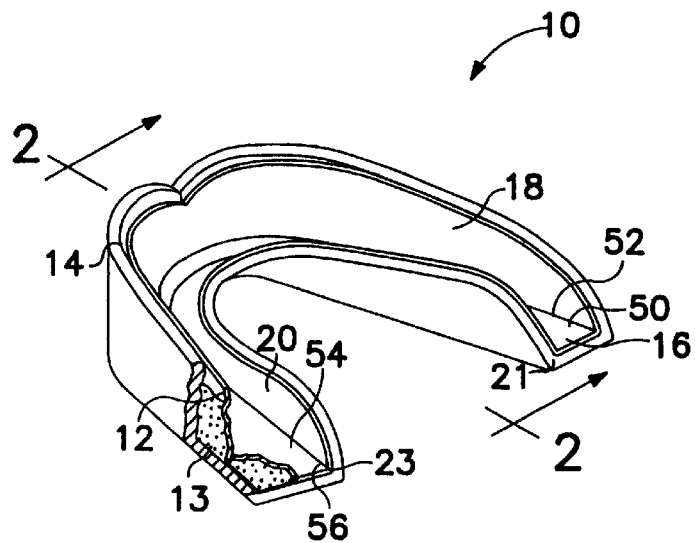
FIG. 1 is an isometric view showing the device assembly according to the present invention.

As has been noted, the non-adhesive carrier for controlled regional release of the present invention may be fabricated from a variety of polymeric materials as long as the material has a network of porous cavities defining a treatment release region. The cavities are sized to incorporate a treatment agent and release that agent over a predetermined period of time.

The polymeric material achieves an equilibrium with the environment in which it is placed. Factors that influence this equilibrium are charge distribution, concentration and molecular weight of the bioactive substance in relation to the pore size of the polymeric carrier. Polymers having the required microporous structure are: silicone, polyurethane, polyvinyl alcohol, polyethylene, biodegradable polylactic acid polymers, polyglycolic acid polymers, polyesters, hydrogels, polytetrafluroethylene, polyfluorosilicones, copolymers and blended mixtures thereof.

One preferred polymer material is a thermoplastic co-polymer made of a ethylene vinyl-acetate with a vinyl acetate proportion in the range of 27.2% to 28.8%, yielding a melt index of 22 to 28 decigrams/minute. A suitable product is Elvax 250 from DuPont. Another preferred polymer is a combination of polycaprolactone, such as Capra 650 from Solvoy-Interox, and an ethylene vinyl-acetate co-polymer, such as Elvax 350 by DuPont.

The treating agent is preferably admixed in the polymer for transfer or elution from the polymer material. The rate of elution of the treating agent is controlled by selecting a pore size for the polymer material in response to the concentration and molecular weight of the treating agent to achieve equilibrium between the polymer and the patient's fluids proximate the polymer. This permits a controlled and prolonged release of the treating agent in its carrier treating fluid in the treatment release region over a predetermined contact time with the users mouth.

The treating agent may be any material that is beneficially employed over extended periods of contact with the patient's mouth, gums and the like. Preferred treating agents are: weak acids for the purpose of softening plaque and other materials that collect on the teeth; tooth de-sensitizing agents; sources of fluoride for treatment of the teeth; saliva control agents; and specific treating agents for specific purposes. Examples of specific treating agents are: citric acid, carbamide peroxide, tetracycline, chlorhexidine, sodium fluoride, and anti-salivating agents. Such anti-salivating agents may be used to prevent excessive salivation in athletes who are engaged in strenuous activities where mouthguards are required, such as hockey, football, basketball and the like. Alternatively, the present invention may be used to treat teeth with fluoride treatments over extended periods of time, as will be shown herein.

A variety of other treating agents may be selected from medical treatment agents such as heparin, hirudin, prostacyclenes and analogs thereof, antithrombogenic agents, chemotherapy agents, steroids, ibuprofen, antimicrobials, antibiotics, and mixtures of bioactive substances for simultaneous multiple treatments, particularly when treatment of the mouth, gums, jaw and related areas are to have direct topical treatment in regions over a prolonged period of time.

EXPERIMENTAL TESTS

To demonstrate the efficacy of the present invention, a plurality of experiments were performed with controlled release of Fluoride for cavity prevention in dental patients. Trays loaded with Sodium Fluoride at 2%, 5%, 10% and 20% by weight were prepared using a carrier tray formed from ethylene vinyl-acetate. The vinyl acetate proportion in the range of 27.2% to 28.8%, yielding a melt index of 22 to 28 decigrams/minute. Elvax 250 from DuPont was used.

The loaded trays were weighed and placed in tubes containing 40 ml of phosphate buffered saline pH (PBS) to simulate saliva conditions in the mouth and incubated at 30° C. under gentle agitation. At each time point, the trays were removed, blotted dry with filter paper, and weighed. The release medium was replaced with fresh PBS, the removed medium stored for analysis and the trays were again incubated at physiological temperature.

To simulate boiling and forming of the tray to the patient's bite, a tray of 5 or 20% sodium fluoride were immersed in 200 ml boiling water for 3–4 seconds, which was long enough to make the Elvax polymer soft, yet not long enough to allow shrinkage. Quickly the tray was placed in a die, clamped, immersed in 500 ml of PBS, and placed in a desiccator under vacuum. Bubbles began to form as the buffer began to degas. After about 30 seconds, the desiccator was opened and the tray removed from the PBS. The procedure allowed the tray to form as in a clinical setting and simulate the suction by the patient while forming the tray to the teeth. Both the boiled water and the PBS were stored for later analysis of fluoride.

Nine ml samples from the above experiments were placed in a scintillation vial. One ml of ionic strength buffer was added. The solution was stirred and a previously calibrated fluoride in-selective electrode was inserted into the vial and the voltage was recorded. A Nernstian response was observed as the voltage was linearly related to me logarithm of fluoride concentration ($10^{-5}$–$10^{-1}$ M, 55–59 mV/decade log concentration) to allow determination of fluoride in the samples. All samples were within the range of detection.

Controlled release of sodium fluoride was observed continuously over a two month period. Presented below in Table I are the results of this observation.

TABLE I

| | milligrams NaF released after number of days | | | |
|---|---|---|---|---|
| NaF, percent | 10 days | 20 days | 35 days | 60 days |
| 2% | 10 | 12 | 13 | 15 |
| 5% | 22 | 27 | 37 | 56 |
| 10% | 35 | 55 | 75 | 105 |
| 20% | 80 | 135 | 165 | 225 |

The amount of sodium fluoride was controlled precisely by how much sodium fluoride was loaded. As is shown in Table II, the fraction fluoride released was independent of loading, within experimental error, indicating that the release mechanism for all the trays was identical. In addition, the pores generated by the loaded salt did not appear to influence the release kinetics as might be expected for the release of large molecules from such a polymer.

TABLE II

| | fraction NaF released after number of days | | | |
|---|---|---|---|---|
| NaF, percent | 10 days | 20 days | 35 days | 60 days |
| 2% | 0.09 | 0.13 | 0.14 | 0.18 |
| 5% | 0.11 | 0.14 | 0.18 | 0.23 |
| 10% | 0.06 | 0.11 | 0.14 | 0.18 |
| 20% | 0.07 | 0.13 | 0.16 | 0.21 |

It was found that the release mechanism obeyed classical square root time dependence, shown in Table III. The fraction released is linearly related to the square root time, which is believed to be consistent with the laws of diffusion.

TABLE III

| | fractional NaF released, square root of days | | | |
|---|---|---|---|---|
| NaF, percent | 2 | 4 | 6 | 8 |
| 2% | 0.05 | 0.11 | 0.14 | 0.19 |
| 5% | 0.05 | 0.10 | 0.16 | 0.23 |
| 10% | 0.04 | 0.09 | 0.14 | 0.19 |
| 20% | 0.05 | 0.10 | 0.15 | 0.21 |

The release kinetics were linked to the rate of water uptake, as shown in Table IV, which was also believed to be controlled by diffusion. The fraction released was correlated with the swelling ratio of wet tray weight/initial dry weight. The most likely mechanism of release is believed to be diffusion of the fluid (water here) through the pores of the polymer followed by osmotic pumping of the sodium fluoride out of the tray.

TABLE IV

| | fraction NaF released vs. Swelling ratio (wet/dry) | | |
|---|---|---|---|
| NaF, percent | 1.0 | 1.1 | 1.2 |
| 2% | 0.0 | 0.10 | 0.15 |
| 5% | 0.0 | 0.11 | 0.18 |
| 10% | 0.0 | 0.09 | 0.19 |
| 20% | 0.0 | 0.12 | 0.22 |

It was found that only small amounts of sodium fluoride were lost during boiling and forming, shown in Table V. Less than 2% of the fluoride was lost during both procedures, and about 0.5–1.0% during each of the simulations normally performed to mold the patient's teeth to the tray.

TABLE V

| | milligrams NaF released | |
|---|---|---|
| NaF, percent | boiled | formed |
| 5% | 2.9 mg | 1.0 mg |
| 20% | 8.9 mg | 6.5 mg |

Figure 3:
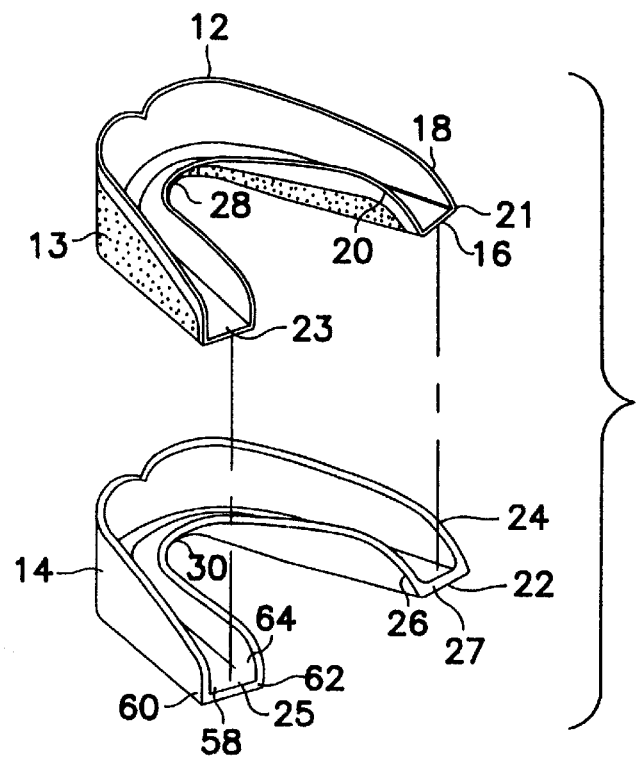
FIG. 3 is an exploded view showing the two components of the device assembly.

A preferred embodiment for the present invention includes a double tray with the two trays being of two different materials. This embodiment is illustrated in the drawings. It should be noted that each of the trays may be used separately for treatments. The inner tray is easily customized to include the treating agent of the present invention, FIG. 1 shows an assembled dental tray device 10 with the inner tray fitted inside the carrier tray 14. FIG. 3 shows the exploded view of the assembly 10. The inner tray 12 is comprised of a bottom wall 16 in a U-shaped configuration generally in the shape of a row of teeth with an outer side wall 18 attached at the bottom surface 50 to the outer edge 52 of the bottom wall 156. The two side walls 18 and 20 and bottom wall 16 form the inner tray 12 in a horseshoe shaped configuration with a U-shaped cross-section open at the ends 21, 23.

The carrier tray 14 is similarly in a horseshoe shaped configuration with a U-shaped cross-section. It is formed by having a bottom wall 22 in a horseshoe shaped configuration, generally in the shape of a row of teeth, whose outer edge 58 is attached to the bottom surface 60 of the outer side wall 24 and whose inner edge 62 is attached to he bottom surface 64 of the inner side wall 26. The U-shaped cross-section is open at the ends 25, 27.

Figure 2:
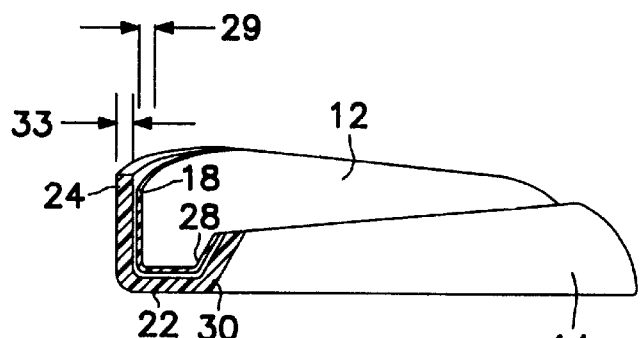
FIG. 2 is a cross-sectional view of the device assembly taken along lines A—A of FIG. 1.

In FIG. 2, the inner tray 12 and carrier tray 14 are shown as a cross-section. Though not to scale, the drawing does illustrate that the wall thickness 29 of the inner tray 12 is less than the thickness 33 of the carrier tray 14. FIG. 2 also illustrates the oblique angle between the inner side walls 20, 26 and the bottom walls 16, 22 at centers 28 and 30. The thinness 29 of the walls of the inner tray 12 is an important feature for the comfortable use, ease of use and successful conforming of the inner tray or use while still producing an accurate, hard, flexible tray. The thinness of the inner tray 12, because it loses the ability to maintain its shape at molding temperatures, is a problem that is resolved by the double tray assembly set forth herein. The carrier tray 14, although moldable in the temperature range of 145°–160° F., has sufficient mechanical integrity to keep the carrier tray 14 and inner tray 12 in their original shapes during heating, handling, insertion into the mouth and molding.

The height of the walls 18, 20 of the inner tray 12, when assembled with the carrier tray 14, are less than the height of the walls 24, 26 of the carrier tray 14. This is to facilitate the use of the carrier tray 14 as a sealing mechanism with the gums to help create the conforming vacuum. The higher walls 24, 26 of the carrier tray 14 will extend beyond the walls 18, 20 of the inner tray 12, to insure that the carrier tray 14, being more flexible and resilient over a wider range of temperatures due to its hardness characteristics, will make and maintain the seal with the gums necessary for the suction forming in the mouth. Additionally, due to the hardness of the inner tray 12 at atmospheric temperature because of its material composition, it is desirable that the walls 18, 20 of the inner tray 12 will not rub on the surface of the gums during wearing. Also because of the dimension 29 of the walls of the inner tray 12, they can be trimmed easily by the use of curved cuticle scissors or other similar instruments.

As described, the preferred embodiment uses the friction fit of the inner tray 12 with the carrier tray 14 to keep the dental tray assembly 10 together during heating, handling and fitting. As an alternative, a suitable, non-solvent, removable adhesive 13 may be applied between the carrier tray 14 and inner tray 12. The adhesive 13 should be selected so as not to interfere with the materials, have adhesive quality during the temperatures of heating and molding, be suitable for use in patient's mouths and have adhesive qualities such that when the inner tray 12 is set and hard, the carrier tray 14 can be peeled away from the inner tray 12 and the adhesive 13 easily removed.

The carrier tray 14 is comprised of a thermoplastic co-polymer made of a ethylene vinyl-acetate with a vinyl acetate proportion in the range of 27.2% to 28.8%, yielding a melt index of 22 to 28 decigrams/minute. A suitable product is Elvax 250 from DuPont.

The inner tray 12 is a combination of polyester resins, co-polymers, and additives made up of the following configuration: 50% to 80% by weight of polycaprolactone, an aliphatic polyester resin with a molecular weight of 40,000 to 80,000, such as Capra 650 from Solvoy-Interox; 10% to 40% by weight of ethylene vinyl-acetate co-polymer with a proportion of vinyl acetate being in the range of 24.3% to 25.7% by weight and a melt index of between 17.3 to 20.9 decigrams/minute, such as Elvax 350 by DuPont; 5% to 10% by weight of silica filler, such as Hisil 233 from PPG Industries; 0% to 1% by weight of primary antioxidant such as Igranox 1010 from Ciba Giege; and 0% to 1% by weight of secondary antioxidant such as Irgaphos 168 form Ciba Giege.

The applicant has found that the following composition is quite suitable for the purposes of the inner tray: approximately 67.19 by weight of polycaprolactone, an aliphatic polyester resin, such as Capra 650 by Solvoy-Interox, approximately 9% by weight of ethylene vinyl-acetate co-polymer such as Elvax 350 by DuPont, approximately 9% by weight polystyrene butadiene co-polymer such as Stereon 840A by Firestone, approximately 13% by weight of silica filler, such as Hisil 233 by PPG Industries, approximately 0.2% by weight of a primary antioxidant, such as Ingranox 1010 from Ciba Giege, and approximately 0.2% by weight of a secondary antioxidant such as Igraphos 168 from Ciba Giege.

The wall thickness of the carrier tray 14 is thicker than the inner tray 12. Because the carrier tray 14 is thicker and because of the material used, it retains more shape integrity at the temperatures used in heating the dual trays. Thus, it gives mechanical support to the inner tray 12 to retain the inner tray's 12 basic shape while being heated, handled and inserted in the mouth. Without the carrier tray 14, the inner tray 12 would be very difficult to work with and to properly insert in the mouth.

The carrier tray 14 also provides another benefit. In the heating process, both trays are heated to between 145°–160° F. During the time from removal of the dual tray assembly 10 from the hot liquid bath until it is inserted in the mouth at a temperature that is not hot enough to cause injury or be uncomfortable, very little heat will be lost, leaving the inner tray 12 in a pliable and formable condition. The forming of the inner tray 12 will be accompanied by the vacuum formed by sucking and pressure. There will be a reasonable time for forming because the tray assembly 10 of the carrier tray 14 and the inner tray 12 will have retained heat, much more than the inner tray 12 alone. Thus the carrier tray 14 will act as a heat sink for the dual trays 10 during forming, extending the period during which the inner tray 12 may be worked into a conformed impression of the teeth. The carrier tray 14 thus performs two functions. One, to give mechanical strength and body to the inner tray 12, and the second to extend the period of time that the inner tray 12 stays in a softened state.

As an alternative embodiment, the dual tray assembly may be held together during the heating and molding process by a suitable adhesive 13 as described before.

In the heating and preparation of the dual dental tray assembly 10, a useful heating method is to use a common water heating apparatus such as a drip coffee maker (not shown). The water is heated to a suitable temperature and goes into the basket where the assembly 10 is placed. The basket arrangement is sterile, in that it is used only for new dual dental tray assemblies 10. When the assembly 10 is sufficiently heated, the assembly 10 is either placed in the mouth for forming or it can be placed in a container of hot water, to keep it at a suitable temperature until it is ready to use. The coffee carafe that has captured the heated water draining from the basket can be that container. Additionally, if during fitting it is determined that the dual dental trays need to be reheated, the carafe of hot water can be used without risk of contaminating the basket area. After the forming, the carafe water is discarded. The carafe can then be sterilized for new patients.

After the dual tray assembly 10 is removed from the mouth, the assembly 10 is cooled, either by placing in cold water or in the air. At cooled temperatures, the inner tray 12 will be hard and retain the shape of the teeth. The carrier tray 14 will be flexible and resilient.

Once the dual trays are cool, the carrier tray 14, with or without the adhesive, is peeled from the inner tray 12. Any remaining adhesive 13 is removed from the inner tray 12 and the carrier tray 14.

The inner tray is now ready for use. The carrier tray 14 may be kept by the patient for any subsequent fittings of inner trays 12 due to dental changes or need to replace the formed inner tray 12. Also, the carrier tray 14 is usable as a dental tray to apply fluoride get, which may be necessary to desensitize the teeth after a bleaching treatment.

While particular embodiments of the present invention have been illustrated and described, it is not intended to limit the invention, except as defined by the following claims.

We claim:

1. A dual tray assembly useful for delivering a predetermined treatment agent to a major region of a user's mouth, comprising:

an outer tray with a horseshoe shaped configuration having an open U-shaped cross section; and means for forming a non-adhesive mouthguard carrier for controlled regional release, said carrier means being formed from a polymeric material having a network of porous cavities defining a treatment release region, said cavities being sized to incorporate a treatment agent and release said agent over a predetermined period of time, said carrier comprising an inner tray with a horseshoe shaped configuration having an open U-shaped cross section which extends over the teeth that removably nests inside the outer carrier tray making a dual tray assembly; the inner tray being made of a thermoplastic compound that is soft and pliable at elevated temperatures but is hard and flexible at body temperatures after the dual tray assembly at elevated temperature is placed in the patient's mouth and is conformed by pressure applied to the inner tray through the dual tray assembly; and a treating agent in a treating fluid for release from said porous cavities in said treatment release region to provide for release of said agent over a predetermined contact time with a substantial portion of the users mouth, said agent having a molecular weight and concentration in said treating fluid such that the specific rate of release of said agent is controlled by the relationship of the molecular weight and molecule size of said agent, the cavity dimensions, and the specific properties of the carrying fluid.

2. The assembly of claim 1, wherein said inner tray has a thickness small enough for said outer carrier tray to replicate said conformation to the teeth and said outer carrier tray is made of a thermoplastic material that is soft at elevated temperatures so as to conform to said inner tray when said inner tray is being conformed to said set of teeth being modeled.

3. The dual tray assembly of claim 1, wherein the inner tray is pliable at temperatures between 145°–160° F.

4. The dual tray assembly of claim 1, wherein said inner tray is hard at temperatures below 120° F.

5. The dual tray assembly of claim 1, wherein said inner tray can be repeatedly molded to the shape of the patient's teeth.

6. The dual tray assembly of claim 1, wherein said outer carrier tray wall is thicker than said inner tray wall.

7. The dual tray assembly of claim 6, wherein said inner tray has a wall thickness between 0.25 mm and 1.25 mm.

8. The dual tray assembly of claim 1, wherein said inner tray material includes polycaprolactone polymer.

9. The dual tray assembly of claim 8, wherein said inner tray thermoplastic material is principally polycaprolactone polymer.

10. The device of claim 1, wherein said specific properties of said treating fluid comprise its surface tension and viscosity.

11. The device of claim 1, wherein said properties further include the degree of solubility of said agent in said fluid.

12. The device of claim 1, wherein said agent is a source of fluoride for treatment of said teeth.

13. The device of claim 1, wherein said agent is a saliva control agent.

14. A dual tray assembly useful for delivering a predetermined treatment agent to a major region of a user's mouth, comprising:

a carrier tray configured generally to conform to a patient's teeth; and means for forming a non-adhesive mouthguard carrier for controlled regional release, said carrier means being formed from a thermoplastic compound including 50% to 80% by weight polycaprolactone and 10% to 40% by weight of ethylene vinyl-acetate, said compound having a network of porous cavities defining a treatment release region, said cavities being sized to incorporate a treatment agent and release said agent over a predetermined period of time, said carrier comprising an inner tray with a horseshoe shaped configuration having an open U-shaped cross section which extends over the teeth that removably nests inside the carrier tray making a dual tray assembly; and a treating agent in a treating fluid for release from said porous cavities in said treatment release region to provide for release of said agent over a predetermined contact time with a substantial portion of the users mouth, said agent having a molecular weight and concentration in said treating fluid such that the specific rate of release of said agent is controlled by the relationship of the molecular weight and molecule size of said agent, the cavity dimensions, and the specific properties of the treating fluid.

15. The assembly of claim 14, wherein said polycaprolactone has a molecular weight ranging from 40,000 to 80,000.

16. The assembly of claim 14, wherein said ethylene vinyl-acetate has a proportion of vinyl acetate ranging from 24.3% to 25.7% by weight and a melt index between about 17.3 and 20.9 decigrams/minute.

17. The assembly of claim 14, wherein said inner tray further includes 5% to 10% by weight of a polystyrene butadiene copolymer.

18. The assembly of claim 14, wherein said inner tray further includes 1% to 15% silica filler.

19. The assembly of claim 14, wherein said carrier tray is made from an ethylene vinyl-acetate.

20. The device of claim 14, wherein said specific properties of said treating fluid comprise its surface tension and viscosity.

21. The device of claim 14, wherein said properties further include the degree of solubility of said agent in said fluid.

22. The device of claim 14, wherein said agent is a source of fluoride for treatment of said teeth.

23. The device of claim 14, wherein said agent is a saliva control agent.

24. A dual tray assembly useful for delivering a predetermined treatment agent to a major region of a user's mouth, comprising:

an outer tray with a horseshoe shaped configuration having an open U-shaped cross section; and a non-adhesive mouthguard carrier for controlled regional release, said carrier being formed from a polymeric material having a network of porous cavities defining a treatment release region, said cavities being sized to incorporate a treatment agent and release said agent over a predetermined period of time, said carrier comprising an inner tray with a horseshoe shaped configuration having an open U-shaped cross section which extends over the teeth that removably nests inside the outer carrier tray making a dual tray assembly; the inner tray being made of a thermoplastic compound that is soft and pliable at elevated temperatures but is hard and flexible at body temperatures after the dual tray assembly at elevated temperature is placed in the patient's mouth and is conformed by pressure applied to the inner tray through the dual tray assembly; and a treating agent in a treating fluid for release from said porous cavities in said treatment release region to provide for release of said agent over a predetermined contact time with a substantial portion of the users mouth, said agent having a molecular weight and concentration in said treating fluid such that the specific rate of release of said agent is controlled by the relationship of the molecular weight and molecule size of said agent, the cavity dimensions, and the specific properties of the carrying fluid.

25. The assembly of claim 24, wherein said inner tray has a thickness small enough for said outer carrier tray to replicate said conformation to the teeth and said outer carrier tray is made of a thermoplastic material that is soft at elevated temperatures so as to conform to said inner tray when said inner tray is being conformed to said set of teeth being modeled.

26. The dual tray assembly of claim 24, wherein the inner tray is pliable at temperatures between 145°–160° F. and hard at temperatures below 120° F.

27. The dual tray assembly of claim 24, wherein said outer carrier tray wall is thicker than said inner tray wall and wherein said inner tray material includes polycaprolactone polymer.

28. The dual tray assembly of claim 24, wherein said specific properties of said carrying fluid comprise its surface tension and viscosity.

29. The device of claim 24, wherein said agent is selected from the group consisting of a source of fluoride for treatment of said teeth and a saliva control agent.

* * * * *